United States Patent
Szanto et al.

(10) Patent No.: US 8,915,922 B2
(45) Date of Patent: Dec. 23, 2014

(54) METHOD OF PLANNING AND PERFORMING A SPHERICAL OSTEOTOMY USING THE 3-DIMENSIONAL CENTER OF ROTATION OF ANGULATION (CORA)

(75) Inventors: Zsigmond Szanto, Twin Falls, ID (US); Noel Fitzpatrick, Surrey (GB)

(73) Assignee: Zsigmond Szanto, Twin Falls, ID (US)

( * ) Notice: Subject to any disclaimer, the term of this patent is extended or adjusted under 35 U.S.C. 154(b) by 401 days.

(21) Appl. No.: 13/413,541

(22) Filed: Mar. 6, 2012

(65) Prior Publication Data

US 2012/0215227 A1 Aug. 23, 2012

Related U.S. Application Data

(60) Continuation-in-part of application No. 13/136,243, filed on Jul. 26, 2011, now Pat. No. 8,518,045, which is a division of application No. 12/211,063, filed on Sep. 15, 2008, now Pat. No. 8,535,317.

(60) Provisional application No. 60/993,820, filed on Sep. 13, 2007, provisional application No. 61/450,062, filed on Mar. 7, 2011.

(51) Int. Cl.
| | |
|---|---|
| A61F 5/00 | (2006.01) |
| A61B 17/58 | (2006.01) |
| A61B 17/14 | (2006.01) |
| A61B 17/16 | (2006.01) |
| A61B 17/15 | (2006.01) |
| A61B 19/00 | (2006.01) |

(52) U.S. Cl.
CPC ........... *A61B 17/14* (2013.01); *A61B 2019/502* (2013.01); *A61B 2019/505* (2013.01); *A61B 19/50* (2013.01); *A61B 17/141* (2013.01); *A61B 17/1637* (2013.01); *A61B 17/151* (2013.01)
USPC .......................................................... 606/87

(58) Field of Classification Search
USPC ...................... 606/79–85, 86 R, 87
See application file for complete search history.

(56) References Cited

U.S. PATENT DOCUMENTS

| | | | |
|---|---|---|---|
| 2,210,623 A | 8/1940 | Kelly | ............................. 425/277 |
| 4,069,824 A | 1/1978 | Weinstock | |

(Continued)

FOREIGN PATENT DOCUMENTS

| | | | | |
|---|---|---|---|---|
| DE | 19723718 A | 12/1998 | ................ B23B 5/36 |
| WO | WO 2006-059120 | 6/2006 | |

(Continued)

OTHER PUBLICATIONS

Fox, et al.; Principles of Uniapical and Biapical Radial Deformity Correction Using Dome Osteotomies and the Center of Rotation of Angulation Methodology in Dogs. Abstract, DerekB. Fox, DVM, PhD, Diplomate ACVS, James L. Tomlinson, DVM, MVSci, Diplomats ACVS, James L. Cook, DVM, PhD, Diplomate ACVS, and Lee M. Breshears, DVM. Veterinary Surgery, 35:67-77, 2006.

(Continued)

*Primary Examiner* — Nicholas Woodall
(74) *Attorney, Agent, or Firm* — TraskBritt, P.C.

(57) ABSTRACT

A pre-surgical planning method for performing a spherical osteotomy for the surgical sectioning of a bone includes obtaining a CT scan of a bone. Subsequently manipulating the scan into a three-dimensional CAD format. Utilizing the scan to identify one or more centers of bone correction or 3D CORAs. A surface, configured in the shape of a portion of a sphere, e.g., a semisphere, is then superimposed on the computer representation of the bone. The center of the surface is positioned at a respective center of bone correction. The intersection of the surface and the bone defines a sectioning surface along which the bone is to be cut. Simulating a sectioning of the bone along the sectioning surface and the subsequent realignment of the bone in an optimal configuration using the computer is then performed. The computer simulation is then utilized as a guide for actually sectioning the bone.

36 Claims, 13 Drawing Sheets

(56) References Cited

U.S. PATENT DOCUMENTS

| | | | |
|---|---|---|---|
| 4,349,058 A | 9/1982 | Camparetto | |
| 4,952,214 A | 8/1990 | Comparetto | |
| 4,955,888 A | 9/1990 | Slocum | |
| 5,122,142 A | 6/1992 | Pascaloff | 606/82 |
| 5,169,401 A | 12/1992 | Lester et al. | 606/79 |
| 5,318,570 A | 6/1994 | Hood et al. | 606/99 |
| 5,514,141 A | 5/1996 | Prizzi, Jr. | 606/810 |
| 5,566,458 A | 10/1996 | Bednar | 30/392 |
| 5,643,270 A | 7/1997 | Combs | |
| 5,682,886 A | 11/1997 | Delp et al. | |
| 6,190,390 B1 | 2/2001 | McAllister | |
| 6,238,126 B1 | 5/2001 | Dall | |
| 6,375,684 B1 | 4/2002 | Kriek | |
| 6,485,495 B1 | 11/2002 | Jenkinson | |
| 7,189,036 B1 | 3/2007 | Watson | 408/204 |
| 8,518,045 B2 | 8/2013 | Szanto | |
| 8,535,317 B2 | 9/2013 | Szanto | |
| 8,702,712 B2* | 4/2014 | Jordan et al. | 606/86 R |
| 2004/0236424 A1* | 11/2004 | Berez et al. | 623/14.12 |
| 2005/0130774 A1 | 6/2005 | Wohlfeil et al. | 473/583 |
| 2005/0273112 A1 | 12/2005 | McNamara | |
| 2006/0229621 A1 | 10/2006 | Cadmus | |
| 2008/0287954 A1 | 11/2008 | Kunz et al. | |
| 2008/0312659 A1* | 12/2008 | Metzger et al. | 606/87 |
| 2009/0076513 A1 | 3/2009 | Szanto | |
| 2010/0234844 A1 | 9/2010 | Edelhauser et al. | |

FOREIGN PATENT DOCUMENTS

| | | |
|---|---|---|
| WO | WO 2009/035670 A2 | 3/2009 |
| WO | WO 2009/035670 A3 | 3/2009 |
| WO | WO 2012/134737 | 10/2012 |

OTHER PUBLICATIONS

International Preliminary Report on Patentability for PCT/US2008/010672, mailed Mar. 25, 2010, 9 pages.

Introduction to Spherical Geometry (last modified Apr. 28, 2011).

PCT International Search Report for International Application No. PCT/US2008/010672, mailed Apr. 13, 2009, 4 pages.

PCT Written Opinion for International Application No. PCT/US2008/010672, mailed Apr. 13, 2009, 6 pages.

Principles of Deformity Correction, Dror Paley, Springer-Verlag, 2003, Berlin Germany.

Spherical Geometry—EscherMath, visited Feb. 31, 2011.

The Geometry of the Sphere 1.-3., visited Feb. 31, 2011.

Weisstein, "Spherical Geometry" from MathWorld-A Wolfram Web Resource, visited Feb. 31, 2011.

U.S. Appl. No. 12/211,063, filed Sep. 15, 2008, Zsigmond Szanto, Spherical Ostetomy Device and Method.

U.S. Appl. No. 13/136,243, filed Jul. 26, 2011, Zsigmond Szanto, Spherical Osteotomy Device and Method.

PCT International Search Report, PCT/US12/27917 dated Jul. 13, 2012.

PCT International Preliminary Report on Patentability, PCT/US12/27917, dated Sep. 10, 2013.

* cited by examiner

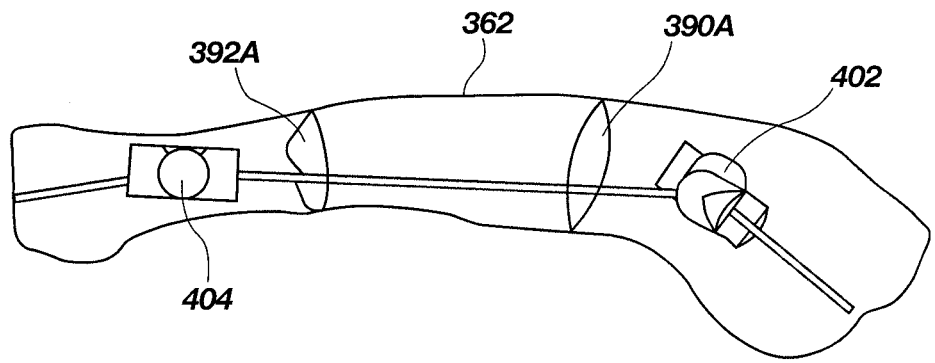
FIG. 8
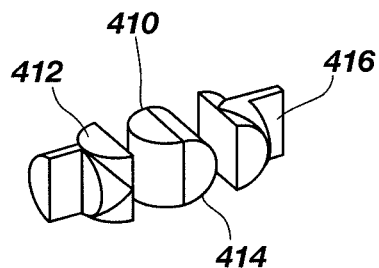 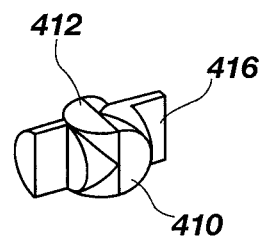 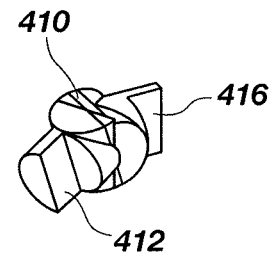
FIG. 9A     FIG. 9B     FIG. 9C
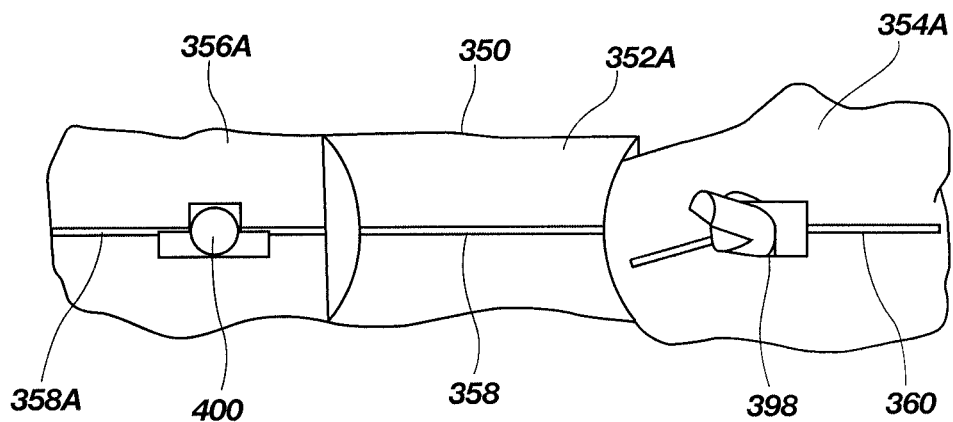
FIG. 10

METHOD OF PLANNING AND PERFORMING A SPHERICAL OSTEOTOMY USING THE 3-DIMENSIONAL CENTER OF ROTATION OF ANGULATION (CORA)

RELATED APPLICATIONS

This application claims the benefit under 35 USC §119(e) of U.S. Application 61/450,062 filed Mar. 7, 2011 for "METHOD OF PERFORMING A SPHERICAL OSTEOTOMY", which is hereby incorporated in its entirety by reference. This patent application is also a continuation-in-part of U.S. application Ser. No. 13/136,243, filed on Jul. 26, 2011, now U.S. Pat. No. 8,518,045 (issued Aug. 27, 2013), which application is a divisional of co-pending U.S. patent application Ser. No. 12/211,063, filed Sep. 15, 2008, now U.S. Pat. No. 8,535,317 (issued Sep. 17, 2013), which claims the benefit under 35 USC §119(e) of U.S. Provisional Patent Application Ser. No. 60/993,820 filed Sep. 13, 2007.

TECHNICAL FIELD

This invention relates generally to methods of performing an osteotomy, namely a surgical division or sectioning of a bone. More particularly, the invention is directed to methods for performing a spherical osteotomy, of the type known as a "true dome" osteotomy.

BACKGROUND

Osteotomy is defined as a procedure for surgical division or sectioning of a bone. This procedure is typically utilized by orthopedic surgeons to correct for malalignment and malorientation, including uniapical and multiapical deformities of the bone, as well as the treatment for compartmental diseases. Bone deformities are the result of the continuous response and adaptation of the bone as a living tissue to several external and internal factors, such as physiological forces, alterations due to trauma, tumors, and other conditions. As a result, the shape of the bone can be severely deformed in three dimensions, comprising angulation in the frontal plane, angulation in the sagital plane, and rotation along the bone axis. Moreover, the deformity can be localized at a point, such as those deformities caused by a fracture or those deformities which spread along the bone as exemplified by those caused by a growth defect.

Displacement osteotomy is the surgical division of a bone and shifting of the divided ends to change the alignment of the bone or to alter weight-bearing stresses. The goal of displacement osteotomies is to create congruent matching surfaces to align, stabilize, and maximize contact between the corresponding bone sections. Osteotomies may include a number of different types of bone sectioning procedures that result in two corresponding sections of the bone which are then reoriented until a desired alignment between the bone sections is achieved. In order to improve stability, distribute the load evenly, eliminate abnormal stress, and aid healing, surgeons strive to maximize the match or contact area between two corresponding surfaces when surgically sectioning the bone. Representative types of bone cuts include simple transverse, obliqued cuneiform, stairstep, simple to complex wedges, barrel-vault, and dome shaped cuts. In practice, a surgeon may choose a specific cut configuration in order to achieve a particular reconfiguration of the bone being treated.

Although so-called "dome osteotomy" has been known for decades, the term "dome osteotomy" has been used to refer conventionally to semi-cylinder, i.e., half or part (partially) cylindrical, shaped surgical cuts. Specifically, amongst experts within the field, "cylindrical osteotomy" would be a more accurate descriptor for these types of so-called "dome" osteotomies, as it is well understood by all to be a cylindrically shaped cut. References to spherical osteotomies in the veterinary literature, to date in particular, have been poorly defined at best and misleading at worst. Although a dome descriptor suggests a truly spherical surface, dome osteotomies as referred to in both human and veterinary orthopedic literature have constituted cylindrical or crescent bone cuts. Although resulting shapes of so-called "dome" osteotomy are not domes, the following terms have been used in the scientific literature to refer to osteotomies wherein corresponding bone cuts are shaped like a semi-cylinder: dome, spherical, barrel-vault, focal dome (reversed dome), crescentic, and arcuate. These conventional forms of semi-cylindrically shaped osteotomies are better described as barrel-vault osteotomies, and will be described accordingly herein below. Further, the term "dome osteotomy" has been used in the literature and within the field of corrective osteotomy to describe barrel-vault osteotomy, however, the field of corrective osteotomy has lacked a method and device to accomplish, as described below with respect to the invention herein presented, what will be termed "true dome" or spherical osteotomy.

In barrel-vault osteotomy, a bone is sectioned by oscillating a saw blade around the central axis of the cylinder while cutting the bone. Barrel-vault osteotomy may be used to correct angulation about the central axis of the cylindrical cut and translation along the central axis of the cylindrical cut. The barrel-vault osteotomy provides and allows correction in two-dimensions, which sometimes results in undesirable secondary translation because of imparted limitation of two-dimensional repositioning of the bone portions. In this respect, barrel-vault osteotomy cannot be used to correct axial rotations of the bone without creating gaps and instability between bone segments thereby being a major limitation of so-called "barrel-vault" osteotomies. The success of barrel-vault osteotomies relies heavily on meticulous pre-operative planning, and while it may be used to correct radial deformities in the frontal and sagittal planes, one of its major disadvantages is the limited ability to correct axial rotational deformities. Accordingly, it would be desirable to provide a device capable of cutting a bone into corresponding sections that allows for correction in more than two-dimensions.

There are a variety of devices and methods available to accomplish these so-called "barrel-vault" osteotomies. One method includes drilling a series of holes in the bone along a planned arc. In one example, U.S. Pat. No. 6,190,390 discloses an apparatus and method for the surgical realignment of the knee through proximal tibial osteotomy. The apparatus has an arcuate profile configuration for establishing a series of parallel holes forming the desired semi-cylindrical contour of the barrel-vault cut. In addition to the general disadvantages of "barrel-vault" osteotomies mentioned above, such a method undesirably creates ridges between adjacent sets of drilled parallel holes making alignment more difficult and gaps between bone portions more probable.

According to another example, U.S. Pat. No. 4,955,888 discloses a biradial saw blade with an arcuate body, powered by oscillating motion that is used to create the barrel-vault osteotomy. Such saw blades are typically associated with a saw assembly which operates to displace the blade in a reciprocating motion by oscillating the blade around the drive axis of the saw assembly. The saw blade has a curved cutting edge at the end of the body shaped as a part of a cylinder for making barrel-vault shaped surgical cuts. While the cut resulting from the use of the biradial saw blade provides for a better match of the two surfaces of both bone portions, the heat and friction produced by the saw blade may be detrimental to the bone, specifically for allowing proper healing thereof. Also, other conventional "barrel-vault" saw blades may include a partially cylindrically shaped body having a cutting member on its leading edge.

Conventional blades are limited in providing semi-cylindrical cuts of the bone which limit the correction in the bone, particularly when correcting deformities that lie in two planes, such as the frontal and sagittal planes. Correction of deformities in two planes requires meticulous preoperative planning in order to determine the central axis about which the cut in the bone is to be made. This is especially crucial if the bone portions are to be properly positioned to correct the deformity. Cutting the bone about a different central axis will only allow, at best, partial correction in the two planes. Further, it is desirable to provide improvement for the correction of malalignment, malorientation, and compartmental disease, including other deformities of the bone by osteotomy procedures and tools. Accordingly, it would be desirable to provide an osteotomy tool for cutting bone that increases the adjustability of the bone portions, achieves optimal bone contact, and improves primary stability. It is also desirable to provide an osteotomy tool that is less dependent upon cutting the bone precisely about a determined central axis when attempting to achieve proper correction.

Another disadvantage associated with the use of so-called "barrel-vault" osteotomies is the limited ability to correct axial rotational deformities. Correction of other deformities may also be difficult to make, particularly when a correction of the deformity requires cutting the bone in a less accessible location. This makes it increasingly difficult for a surgeon to provide the corrective cut, as described above, where it is needed. Another disadvantage of barrel-vault osteotomies is the bone portions, after severance, may only be repositioned with respect to one another about two principal dimensions, one of the principal dimensions being an angular displacement or rotation about the central axis, and the other principal dimension being a lateral displacement or position along the central axis. The angular displacement or rotation allows the bone pieces to be rotated with respect to one another about the central axis to the desired correction. The lateral displacement or position allows the bone pieces to be positioned with respect to each other along the central axis to the desired correction. Also, the bone pieces may obtain the desired correction through a small combination of lateral displacements and angular displacements. Lateral displacement of the bone pieces is limited to the extent that the bone portions include sufficient surface contact for proper healing to occur. Angular displacement of the bone pieces provides for better bone-to-bone contact than lateral displacement, however, angular displacement is still limited if the bone portions are to be maintained with sufficient surface contact in order to provide for proper healing.

A dome saw blade for the execution of true spherical osteotomies has been made available under the trade designation DOMESAW by Matrix Orthopedics of Twin Falls, Id., however guidelines for spherical osteotomy preoperative analysis and planning using the osteotomy rule for spherical true dome osteotomies, the three-dimensional center of rotation and angulation (3D CORA), and 3D computer modeling have not been fully established. The traditional approach for osteomotic procedures as represented by the Paley rules are limited to techniques for performing two-dimensional cuts. Paley's rules, as articulated in Principles of Deformity Correction, D. Paley, Springer-Verlag, Berlin Pg 99-113 (2005), have not been updated to encompass the three-dimensional concept of a true spherical osteotomy (TSO). It follows that there is a need to provide a new method for preoperative analysis and planning of osteotomies directed to achieving true dome ostoetomies.

Current techniques of surgical planning for deformity correction typically include the taking of measurements of the bone from orthogonal X-ray projections and the computation of the angle to be corrected based on these measurements. The efficacy of the results achieved through the conventional process depends on the accuracy of the projections, the plane of the X-ray relative to the deformity to be corrected, the care taken in performing the measurements in the radiograph, and the accuracy of the calculations which are subsequently performed. Moreover, the figures of angulation and rotation obtained with this method can only be verified with the same procedure, performed through the use of different radiographs.

The use of two-dimensional images in the conventional process introduces a number of uncertainties into the planning process, including the difficulty of evaluating bone deformities in all directions and projections.

It would be desirable to provide a method for cutting a bone into corresponding sections resulting in a "true dome" or spherical osteotomy.

It would also be desirable to provide an osteotomy method for "true dome" or spherical osteotomies that would produce two substantially congruent (one concave and one convex) surfaces after the sectioning of the bone.

Furthermore, it is also desirable to provide a method which reduces, if not eliminates, the uncertainties associated with planning a surgical procedure from the limited perspective of two-dimensional images. It would be desirable if the new method would facilitate the three-dimensional evaluation of bone deformities from a number of perspectives and projections would permit the identification of optimal locations for performing a bone sectioning procedure, would establish an optimized angular orientation to which the sectioned bone may be realigned, and would furthermore simulate the result of the completed surgery. Optimally, the new pre-surgical analysis and planning method would perform all of these functions through a methodology which is interactive and capable of producing instant feedback to the clinician charged with the planning of the surgical procedure.

BRIEF SUMMARY OF THE INVENTION

The inventive method presented herein provides a means of producing substantially spherical or "true dome" sectioned surfaces in a bone to be treated, thereby facilitating an optimized correction and realignment of the sectioned bone in three dimensions and subsequently aiding the healing process of the sectioned bone.

In embodiments of the inventive method, a "true dome" or spherical osteotomy device may be used to section a bone into two substantially mating segments, thereby allowing a correction of the bone to be accomplished by rotating the two bone segments about their respective substantially mating surfaces. The method allows for correction through axial rotation without any unnecessary secondary translation. Moreover, "true dome" osteotomy provides for three-dimensional adjustability of the bone while maximizing bone-to-bone surface contact and stability. Advantageously, procedures utilizing the spherical osteotomy device require less complex pre-operative planning and provide more accurate correctional capabilities.

Embodiments of the inventive method provide several important advantages. Specifically, a method of performing a "true dome" or spherical osteotomy, including a method of using a spherical osteotomy device, may create dome shaped mating surfaces as opposed to semi-cylindrical cuts, which result from conventional methods. The new method may provide for a matching of the proximal and distal fragments of the osteotomy and may optimize dome height. Furthermore, the new method may minimize bone loss, may decrease the complexity of pre-operative planning, may allow the surgeon to make intraoperative adjustments to attain desired correction, may not unacceptably wedge or heat bone portions during cutting, may avoid unnecessary heat and burning, may minimize damage to bone tissue and the surrounding soft tissue, may avoid metal to metal contact of surgical instruments, and may aid faster and more reliable healing of the bone. As another advantage, the method anticipates the use of a spherical osteotomy device which may be self-guiding and self-centering within the cut being made in the bone, giving the surgeon options in planning the surgical approach around soft tissue structures.

One aspect of the method of the instant inventive pre-surgical analysis and planning method may involve one or more of the following procedural steps:

(1) Obtaining a computerized tomography (CT) scan or Magnetic Resonance Imaging (MRI) scan of the bone to be treated;

(2) Utilizing a computer to convert the said CT or MRI scan into a three-dimensional (3D) format, preferably a computer assisted design (CAD) format;

(3) Utilizing the computer to isolate the 3D representation of the bone to be treated.

(4) Utilizing the 3D representation of the bone to define a plurality of axes within the bone, each axis being positioned within a respective linear region of the subject bone;

(5) Identifying points of intersection of at least two of those axes, and denominating each of those intersections as a center of bone correction or three-dimensional center of rotation and angulation (3D CORA);

(6) Thereafter, utilizing the computer to locate features at one or more of these centers of bone correction;

(7) Utilizing the computer to define a plurality of surfaces, each having a shape substantially semispherical in configuration, on the 3D representation of the bone wherein a respective epicenter or origin of each semispherical configuration is positioned at a respective center of bone correction or 3D CORA;

(8) Utilizing the computer to define an intersection of each such surface with the 3D representation of the bone. The intersection of the surface and the 3D representation of the bone defines a three-dimensional sectioning surface, i.e., a suggested surface over which the bone is to be sectioned.

(9) Utilizing the computer to simulate a sectioning of the bone along one or more of the sectioning surfaces, i.e., along the intersections of the spherical surfaces and the bone, thereby producing a simulated plurality of segmented bone elements;

(10) Utilizing the computer to position a cardan-type joint or similar universal joint at each of the identified centers of bone correction or 3D CORAs;

(11) Utilizing the computer to assist with pre-surgical analysis and calculations, and with developing a pre-surgical plan.

(12) Utilizing the computer to simulate the positioning of adjacently positioned bone segments;

(13) Utilizing the computer analysis and the best judgment of the surgeon to spatially orient the bone segments with respect to one another by modifying the angles of the cardan joints, in order to obtain an acceptable overall simulated alignment for the bone;

(14) Once the computer simulation of the sectioning and realignment of the bone has been completed, utilizing the computer simulation as a guide to permit the clinician to replicate the results of the computer simulation on the actual bone to be treated;

(15) Identifying and locating the center of bone correction, i.e., 3D CORA, in the actual bone;

(16) Locating the sectioning starting point, to the extent possible, on the actual bone;

(17) Utilizing said computer simulation to identify and dimension a osteotomy device suitable to perform the sectioning on the actual bone;

(18) Providing an osteotomy device corresponding to the identification and dimensions according to step 16;

(19) Providing a solid model of the bone to be treated;

(20) Utilizing the results of the 3D computer analysis, replicating the osteotomy on the solid model;

(21) Utilizing the results of the 3D computer analysis, positioning the cutting edge of the blade in such a way that the epicenter of the blade element of the osteotomy device (O) is at, or substantially at, the same location as the center of bone correction or 3D CORA. In some cases the surgeon can choose an off-set 3D CORA to accomplish the osteotomy;

(22) Actuating the osteotomy device and utilizing the osteotomy device to section the bone along a first respective sectioning surface, defined for that particular portion of the bone;

(23) Subsequent to the initial sectioning of the bone along the first sectioning surface, repeating the sectioning operation for each of the remaining centers of bone correction which have been identified for the bone being treated.

(24) Realigning the bone segments, resulting from the sectioning operations, utilizing the computer simulation results as a guide, thereby producing a realigned bone having the configuration suggested by the computer simulation;

(25) Utilizing a 3D measuring device, guide, and jig to realign the bone;

(26) Utilizing the computer simulation of the sectioning procedure to identify fixation devices suitable to securing adjacent bone elements to one another;

(27) Utilizing information provided by the computer simulation, in association with computer aided design manufacturing applications (CAM) to dimension and design custom fixation devices for securing the sectioned bone elements to one another; and

(28) Utilizing appropriate surgical techniques to fixedly secure the various bone elements in the desired orientations.

Advantageously, the instant osteotomy method may be utilized in a variety of surgical procedures beyond "true dome" or spherical osteotomies, such as in operations to repair bone fracture damage in humans and animals.

Other advantages, features and alternative aspects of the invention will become apparent when viewed in light of the detailed description of the various embodiments of the invention when taken in conjunction with the attached drawings and appended claims.

BRIEF DESCRIPTION OF THE DRAWINGS

While the specification concludes with claims particularly pointing out and distinctly claiming that which is regarded as the invention, the advantages of this invention may be more readily ascertained from the following description of the invention when read in conjunction with the accompanying drawings in which:

FIG. 8 is a side view of the second bone of FIG. 2 having cardan joints positioned on the location features;

FIGS. 9A-9C are perspective views of a cardan joint shown in a number of orientations;

FIG. 10 is a side view of the first bone of FIG. 1 shown in a reoriented configuration wherein the first bone has been segmented and the resulting segments having been realigned;

DETAILED DESCRIPTION OF THE INVENTION

Figure 1:
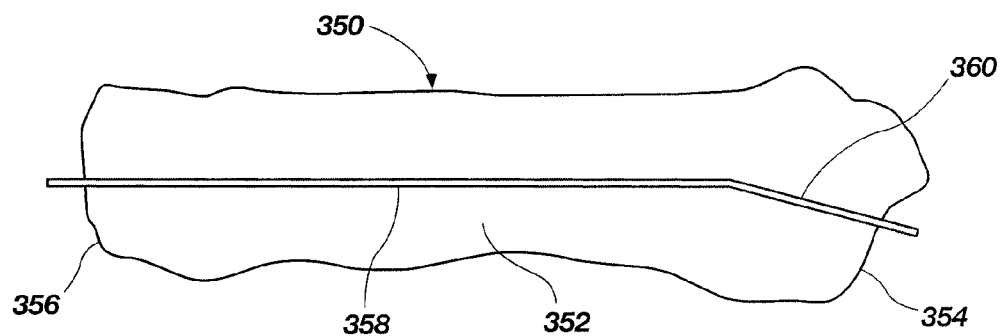
FIG. 1 is a side view of a first bone having two longitudinal axes associated therewith.

The illustrations presented herein are, in some instances, not actual views of any particular osteotomy device, "true dome" osteotomy device, spherical osteotomy device, bone saw bit, cutting element, hard facing material or other feature of an osteotomy bit or device, but are merely idealized representations which are employed to describe the invention. Additionally, like elements and features among the various drawing figures are identified for convenience with the same or similar reference numerals.

"True dome" or spherical osteotomy devices, hereinafter "bone saw bits," suitable for osteotomy or other surgical cutting of bone are presented. Bone saw bits for surgically severing bone are now presented together with some terminology to facilitate a proper understanding of the invention.

The term "spherical" as used herein means a characteristic of a sphere over any portion of a sphere and is not to be limited to a complete sphere, including, but not limited to, a hollow spherical structure. Also, the term "spherical" may refer to an inner surface, an outer surface, or an inner surface and an outer surface of a sphere, including partial portions thereof.

The term "part spherical" as used herein means a characteristic of a sphere or a part sphere over any portion of a sphere and is not to be limited to a sphere or part sphere or a hollow sphere. Also, the term "part spherical" may refer to an inner surface, an outer surface, or an inner surface and an outer surface of a sphere or part sphere, including partial portions thereof.

The term "semispherical" as used herein means a characteristic of a semisphere over any portion of a sphere and is not to be limited to a semisphere. Also, the term "semispherical" may refer to an inner surface, an outer surface, or an inner surface and an outer surface of a semisphere, including partial portions thereof.

As used herein the term "true dome" will be defined as a curved surface, produced by a cutting action, wherein the radius of curvature of that curved surface is constant or substantially constant over the entire curved surface.

As used herein "3D CORA" is defined as the center of rotation and angulation which is established by utilizing a three-dimensional (3D) representation of the bone instead of two-dimensional images based on orthogonal X-ray projections. A 3D CORA allows for defining angular changes in multiple planes.

FIGS. 1-12 illustrate a first aspect of the method of the invention. This particular aspect utilizes a computer to simulate the sectioning and realignment of a bone or limb to be treated prior to the actual sectioning of the bone. The simulation permits the user to define and locate the critical locations on the bone, including the center of bone correction or 3D CORA, as well as the sectioning surface along which the bone is to be sectioned. The simulation permits the user to manipulate the bone to determine the optimal realignment of the sectioned elements of the bone prior to any actual sectioning of the bone being affected.

Under this aspect of the method, a computer tomography (CT) scan of the bone or limb to be treated is first obtained. Production of such a scan is achieved utilizing conventional techniques for creating CT scans. In a preferred approach, a contra-lateral limb may also be included in the scan for purposes of defining a reference point.

Once the scan has been downloaded into a computer, the scan, which may be in a DICOM format, is subsequently converted to a three-dimensional (3D) format, preferably into a 3D computer assisted design (CAD) format. Formats may include but are not limited to those commercially available under the trade designations IGES, Parasolid, and STEP. Alternatively, software specific formats such as SolidWorks, SolidEdge, ProEngineer may be utilized. The process of converting a CT scan to a 3D format is well known in the art and any of the conventionally utilized techniques can be employed for this purpose. Once the scan of the bone has been converted to a 3D format, the bone to be treated is isolated.

Figure 2:
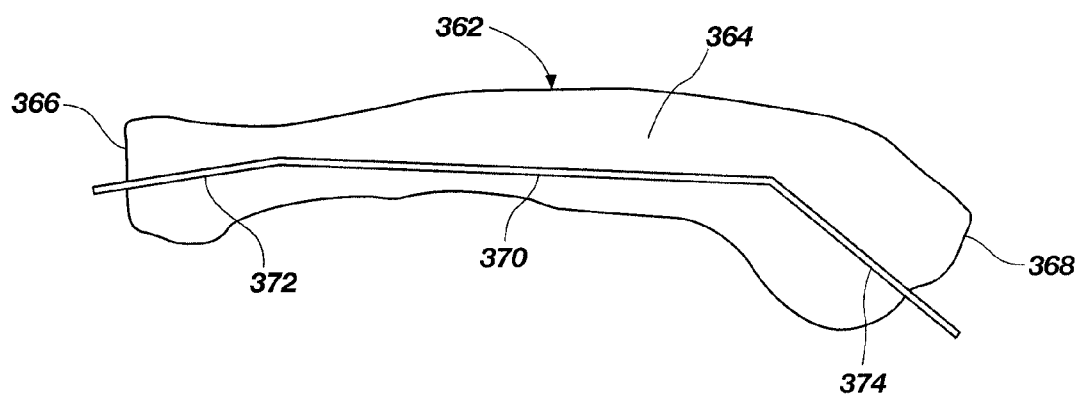
FIG. 2 is a side view of a second bone having three longitudinal axes associated therewith.

Utilizing the multiple views of the bone provided by the 3D model, the clinician identifies a respective longitudinal axis for each substantially linear region of the bone. This identification can be accomplished utilizing conventional engineering techniques for identifying a longitudinal axis for a structural member. In this regard, FIGS. 1 and 2 illustrate two bones which are intended to be treated. The first bone 350 defines a substantially linear region 352 positioned centrally within the length of the bone 350. Bone 350 defines two end sections 354 and 356. The end section 354 is shown as defining a generally linear region of the bone which angles downwardly from the region 352. A first longitudinal axis 358 is defined centrally in the substantially linear region 352. A second longitudinal axis 360 is defined centrally in the substantially linear region of the bone proximate the end 354 of the first bone 350. In FIG. 2 a second bone 362 defines a substantially linear region 364 positioned centrally within the length of the bone and oppositely positioned end regions 366 and 368. A first longitudinal axis 370 extends centrally through the linear region 364 while a second longitudinal axis 372 extends centrally through the region proximate end region 366. A third longitudinal axis 374 extends centrally through the region proximate end region 368.

Figure 3:
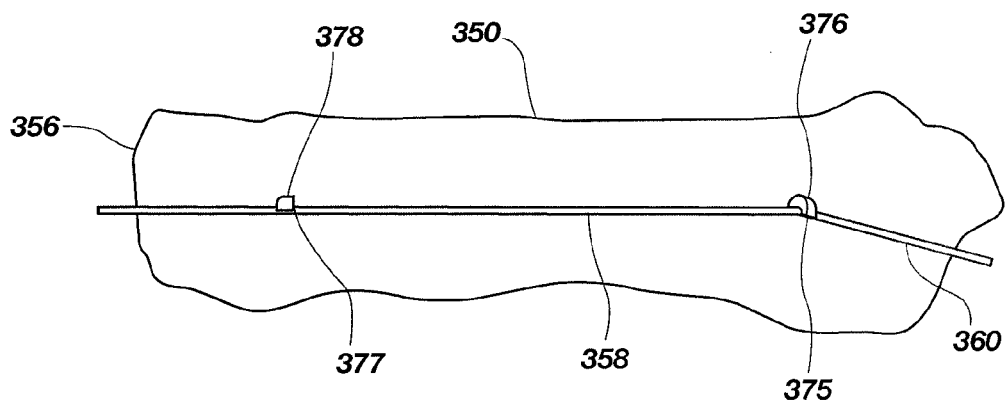
FIG. 3 is a side view of the first bone of FIG. 1 having locating features positioned on the longitudinal axes of the bone.
Figure 4:
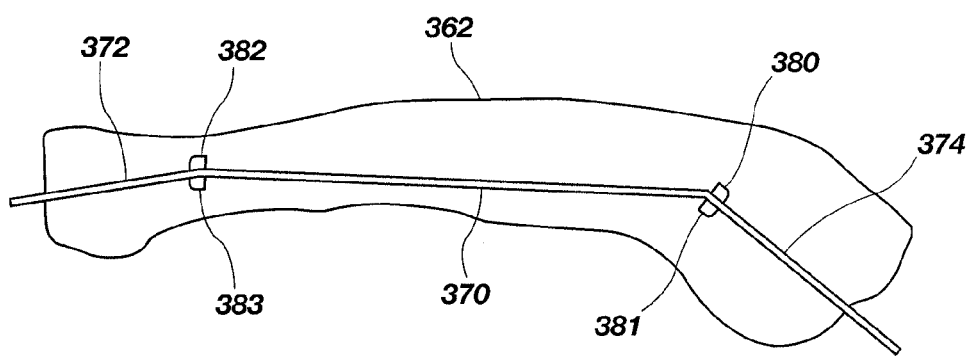
FIG. 4 is a side view of the second bone of FIG. 12 having locating features positioned at the intersections of the axes of the bone.

The point of intersection of two axes defines a center of bone correction or alternatively a CORA, i.e., a center of rotation and angulation. In the present method wherein 3D computer representations are utilized, the intersections are termed 3D CORA's. As shown in FIG. 3 the computer is programmed to define a locator 376, which is defined and positioned at the intersection 375 of the first longitudinal axis 358 and the second longitudinal axis 360. Furthermore, a second locator 378 is shown as being defined and positioned at position 377. Locator 378 is provided to facilitate a realignment of the portion of bone 350 proximate the end 356 of that bone. With reference to FIG. 4, a locator 380 is shown defined and positioned at the intersection of the third longitudinal axis 374 and the first longitudinal axis 370. A second locator 382 is similarly shown as being defined and positioned at an intersection 383 of the second longitudinal axis 372 and the first longitudinal axis 370. These locators are utilized to identify the centers of bone correction or alternatively the 3D CORAs for their respective bone regions.

Figure 5:
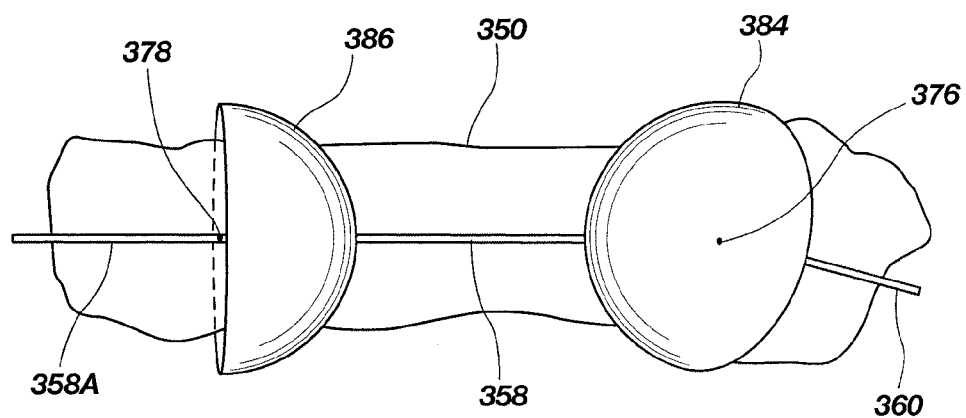
FIG. 5 is a side view of the first bone of FIG. 1 having spherical surfaces centered on the location features of the bone.
Figure 6:
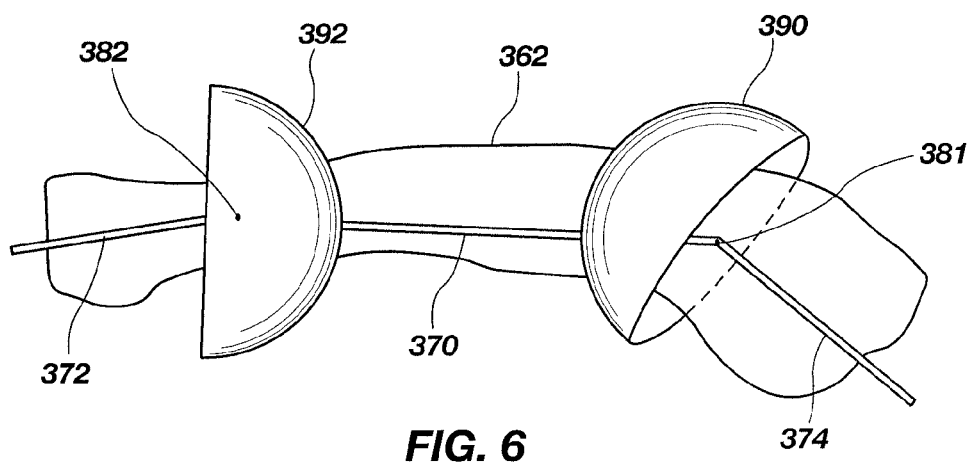
FIG. 6 is a side view of the second bone of FIG. 2 having spherical surfaces centered on the location features of the bone.
Figure 21:
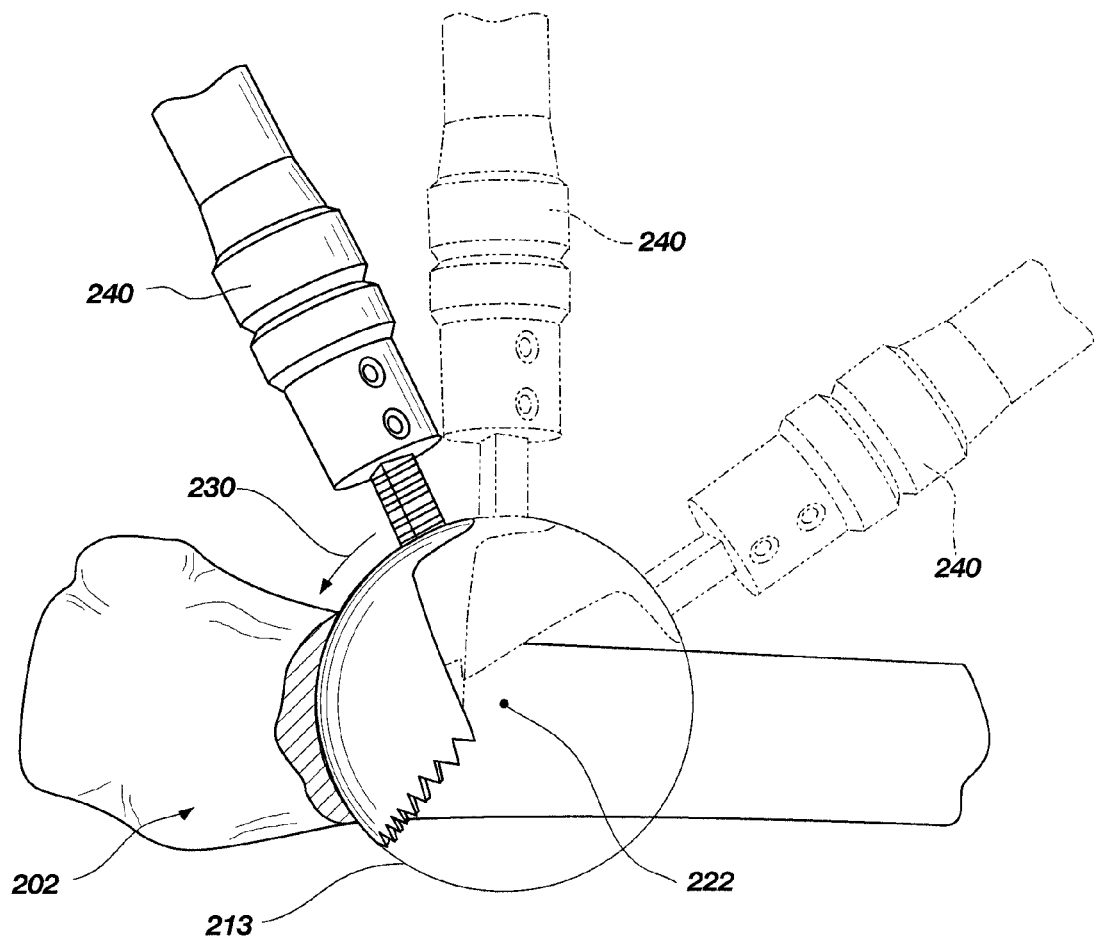
FIG. 21 is a sectional side view of a bone undergoing an osteotomy procedure showing the displacement path of the osteotomy device through the sectioning procedure.

FIGS. 5 and 6 illustrate the placement of a plurality of surfaces, each having a shape which is substantially semispherical in configuration, on the representations of the bones. It should be appreciated that in the actual computer simulation described under this invention, the representation of the bone and the surfaces will be rendered in a three-dimensional format. The semispherical surfaces will therefore be rendered in a three-dimensional representational format. As shown in FIG. 21, a first semispherical surface 384 is positioned over the rightmost portion of the bone such that a center of the semispherical surface is located on the point 376 which also defines the intersection of the two longitudinal axes 358 and 360. The diameter of the surface 384 is dimensioned such that it exceeds the diameter of the bone 350 over the region in which the surface 384 intersects the bone 350. A second semispherical surface 386 is shown positioned proximate the leftmost region of the bone 350 with its origin or epicenter positioned at the location 377 which is also the location of locator 378. Similar to semispherical surface 384, the surface 386 has a diameter which dimensionally exceeds the diameter of the bone over the surface of intersection of the surface 386 with the bone 350.

Although the surfaces 384 and 386 are illustrated as being semispherical in configuration, it should be understood that alternative configurations of these surfaces are within contemplation. Such surfaces may be substantially less than semispherical in configuration, albeit in preferred constructions the surfaces present a shape which includes a portion of a sphere therein.

FIG. 6 likewise illustrates the placement of two semispherical surfaces 390 and 392 over the computer representation of the bone 362. The semispherical surface 390 is shown positioned such that its epicenter or epicenter is positioned at the location 381 which identifies the intersection of the first longitudinal axis 370 and the third longitudinal axis 374. The semispherical surface 392 is positioned such that its origin or epicenter is positioned at the point 382 which is likewise the point of intersection of the first longitudinal axis 370 and the second longitudinal axis 372.

The surface defined by the intersection of each of the surfaces 384, 386, 390 and 392 with their respective bones defines a respective sectioning surface. It is this surface along which the clinician will section the bone to thereby form a series of separate bone elements. Notably, each sectioning surface will have a configuration which represents a portion of a sphere, i.e., a semi spherical surface, due to the configuration of the respective semispherical surfaces whose configurations function to define such section surfaces.

Figure 7:
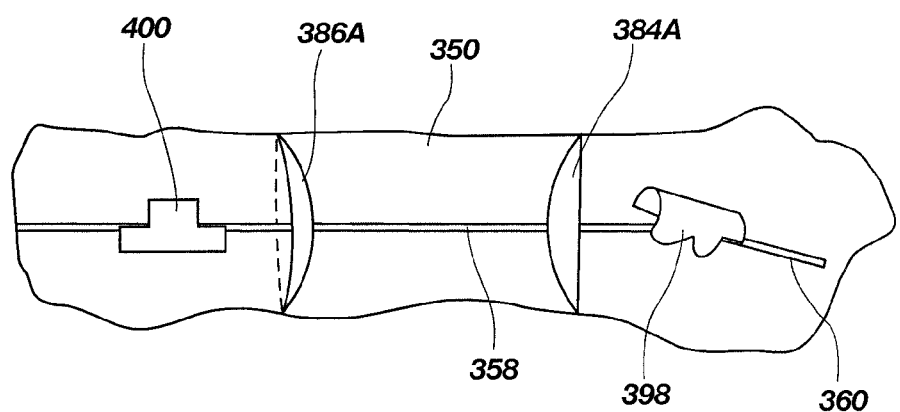
FIG. 7 is a side view of the first bone of FIG. 1 having cardan joints positioned on the location features.

FIGS. 7 and 8 illustrate the two respective bones 350 and 362. Bone 350 is shown with bone sectioning surfaces 384A and 386A while bone 362 is shown with respective bone sectioning surfaces 390A and 392A. A cardan-type joint is shown positioned at each of the locator sites for each bone. In FIG. 7 cardan joint 398 is shown positioned at the location site of locator 376 while cardan type joint 400 is shown positioned at the site of locator 378. Similarly, a cardan type joint 402 is shown located at the site of locator 380 on bone 362 and a cardan type joint 404 is shown located at the site of locator 382. A configuration of a typical cardan type joint which is employed in one aspect of the invention is shown to advantage in FIGS. 9A-9C. As shown, the cardan type joint 410 of the invention is a universal joint formed of two opposing end elements 412 and 416 which are interconnected through a central element 414. The two end elements 412 and 416 may rotate about the central element 414 independent of one another as shown by FIG. 9C. Under the instant method a computer is programmed to permit the user to position a cardan-like joint at the centers of bone correction or 3D CORA and thereby simulate or otherwise duplicate the function of cardan type joints.

Adopting this construct, the clinician is able to rotate the two bone elements, which are positioned about the sectioning surface associated with a respective cardan joint, relative to the cardan joint in order to arrive at an optimized orientation of those two bone elements relative to one another. For example, FIG. 10 illustrates the rotation of the end bone element 354A of bone 350 about cardan joint 398 so as to align the second longitudinal axis 360 of the element 354A substantially with the first longitudinal axis 358 of the central bone element 352A of the bone 350. It is typically the objective of the clinician in this instance to rotate the end bone element 354A about the cardan joint 398 so as to orient the longitudinal axis 360 of the end bone element 354A to be collinear or substantially collinear with the corresponding longitudinal axis 358 of the adjacent bone element, i.e., central bone element 352A. Similarly, the bone element 356A is rotated about the cardan joint 400 so as to align the longitudinal axis 358A of the bone element 356A with the longitudinal axis 358 of bone element 352A. It should be noted that the rotation of the bone elements is effected as the adjacently positioned bone elements are held in contact with one another along the respective ends of the two bone elements which were formed by the sectioning operation. It follows that each pair of adjacently positioned bone elements is held in contact with one another along their abutting ends as one or both of the two elements are rotated about the respective cardan type joint until the desired orientation of their respective longitudinal axes is obtained.

Figure 11:
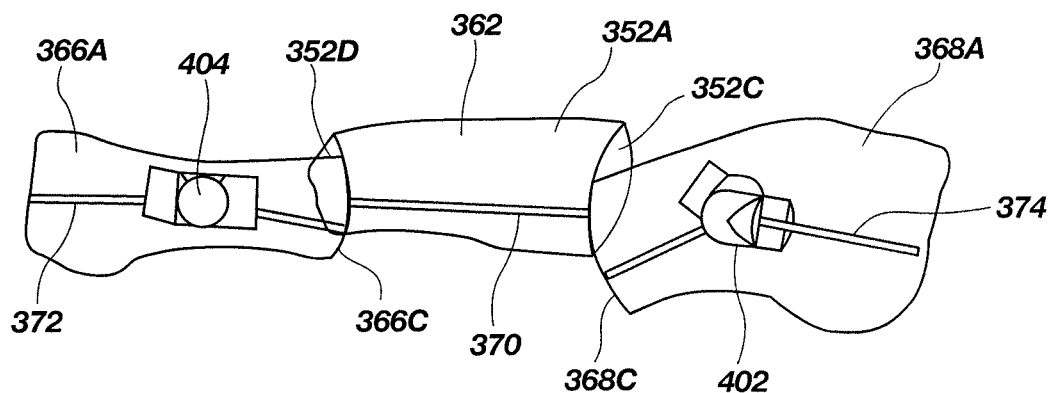
FIG. 11 is a side view of the second bone of FIG. 2 wherein the second bone has been segmented and the resulting segments have been realigned.
Figure 12:
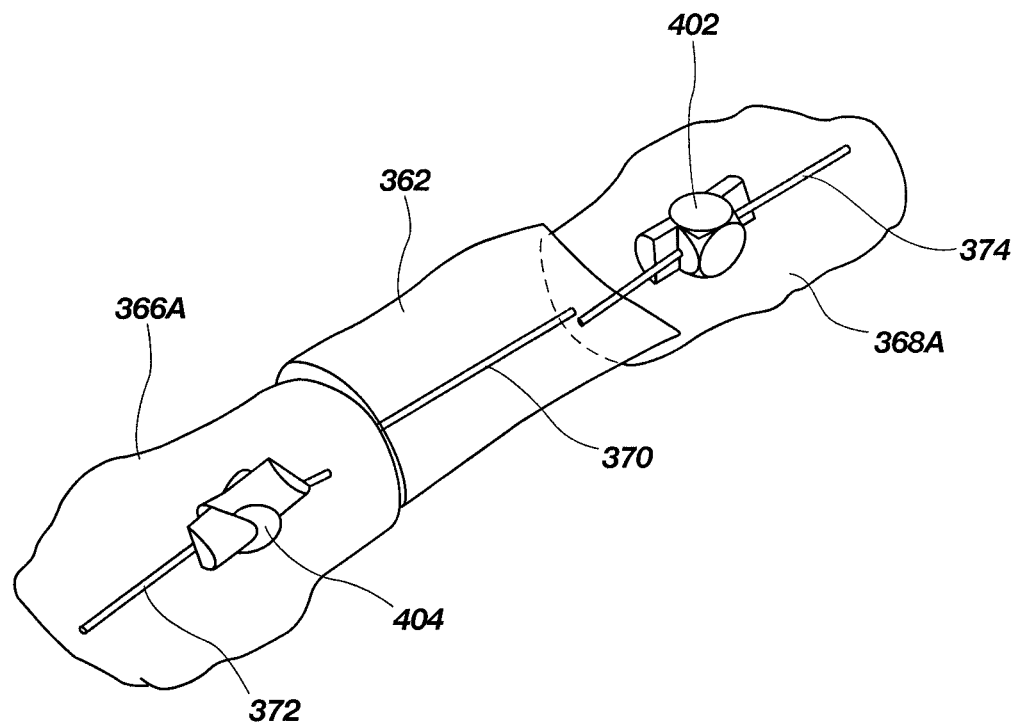
FIG. 12 is a perspective view of the second bone of FIG. 11 showing the orientation of the various bone segments relative to one another.

FIGS. 11 and 12 illustrate the rotation of the bone elements 368A and 366A about the central bone element 352A. As shown bone element 368A is rotated about cardan joint 402 until the longitudinal axis 374 is oriented to be substantially collinear with the longitudinal axis 370 of bone element 352A. During this rotation, the two bone elements 352A and 368A are in continuous abutting contact along the respective end surfaces 352C and 368C of those bone elements. The two end surfaces slide along over the respective surfaces of the opposing bone element during this rotation. Likewise, the bone element 366A is rotated about the cardan joint 404 until the longitudinal axis 372 of the bone element 366A is positioned either collinear or substantially collinear with the longitudinal axis 370 of bone element 352A. During this rotation, the end surface 352D of bone element 352A is held in abutment with the end surface 366C of bone element 366A. As shown in perspective in FIG. 12, the final configuration of the three bone elements presents a construction wherein the respective longitudinal axes of the three bone elements are oriented substantially collinear with one another.

Using the cardan joints permits the clinician to adjust the angulation of the various bone elements in the frontal plane and in the sagital plane. Furthermore, such joints permit the clinician to rotate the bone elements along their respective axes independent of the other bone elements thereby allowing the clinician to fine tune the angle in one projection and then proceed to adjust the angle in another projection knowing that the previous adjustment will remain unaffected. Since the above described procedure is effected utilizing a computer simulation, the clinician is able to continue to manipulate the orientation of the various bone elements until a desirable orientation of the various bone elements is achieved. The use of a three-dimensional format permits the clinician to inspect the configuration of the bone elements from any desired direction or perspective. Further, assuming that the computer programming includes a zoom function, the clinician can utilize such a function to inspect the orientation of the various bone elements with any desired level of magnification.

Correction of angular deformities by osteotomy can be seen as angulating one bone segment relative to another around an imaginary axis line in space. The axis line around which the correction is performed is known as an angulation correction axis (ACA). In performing the alignment of the bone segments under the instant inventive method, the alignment is performed consistent with applicant's newly formulated rule for spherical or true dome osteotomy, namely that the angulation correction axis (ACA) must be through the CORA in the midline bone axis in both sagittal and frontal planes and not any of the bisecting CORAs and the osteotomy must be separated from the CORA by the radius of the blade of the osteotomy device in order for alignment of bone axes to occur.

Once the computer has identified the optimized location and configuration of the section surfaces as well as the optimized realignment of the bone elements to be produced by sectioning along those section surfaces, the information generated by the computer simulation is transferred over to the actual bone to be treated. The surgeon locates the sectioning surfaces on the actual bone and then utilizes an osteotomy device, for example a device as disclosed herein, to section the bone along those section surfaces. Thereafter, the bone elements which result from the sectioning operation are rotated to replicate the orientation specified by the computer simulation. The alignment of the bone elements or segments may be aided by the use of a 3D measuring device, guide, and/or jig to realign the bone. Subsequent to the bone elements being positioned in the desired orientation, conventional surgical techniques are employed to secure the various adjacent pairs of bone elements to one another to form the bone configuration anticipated by the computer simulation.

The instant method utilizes an osteotomy device to perform the actual sectioning of the bone. Various devices are within contemplation for use with the inventive method. The device disclosed in U.S. application Ser. No. 12/211,063, filed 15 Sep. 2008, and entitled SPHERICAL OSTEOTOMY DEVICE AND METHOD may be utilized with the instant method. This pending patent application is incorporated herein by reference in its entirety.

Figure 13:
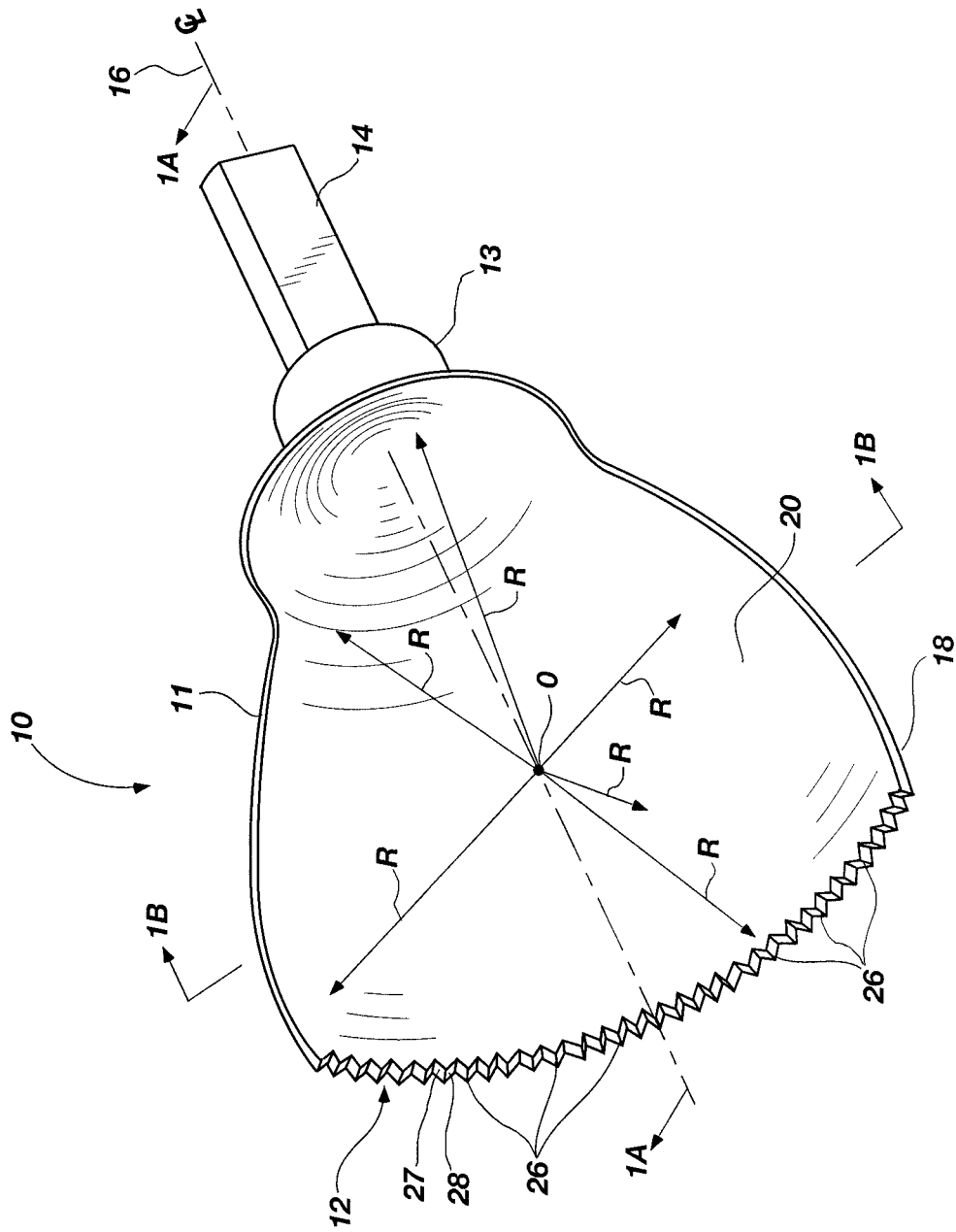
FIG. 13 is a perspective view of a bone saw bit which may be utilized in accordance with an aspect of the invention.
Figure 14:
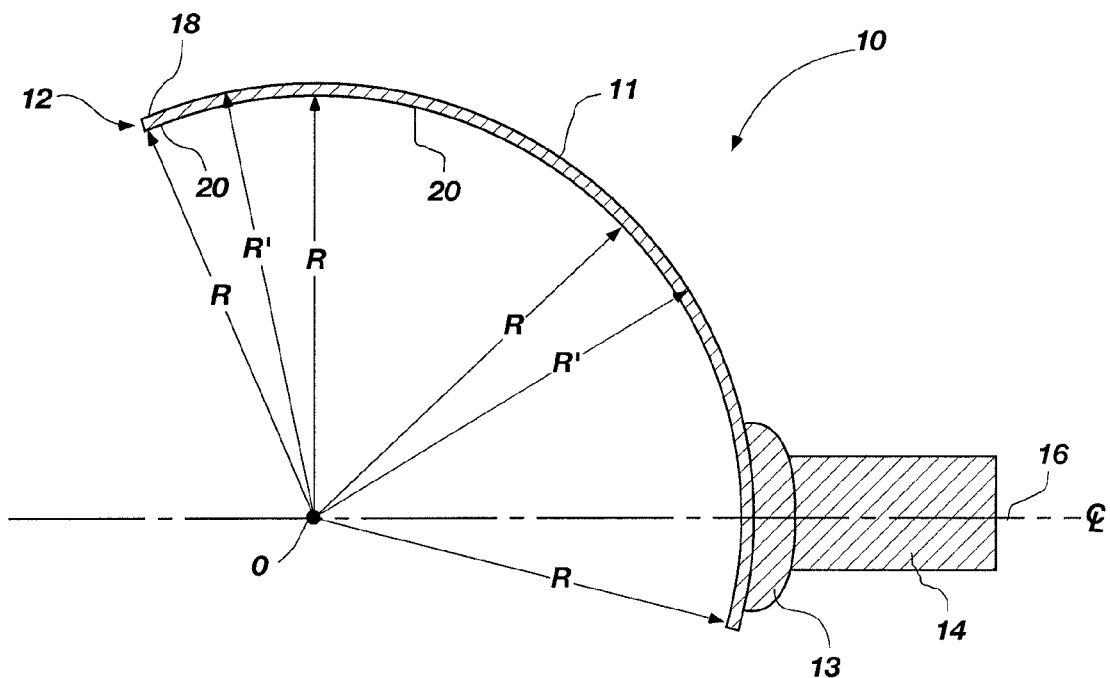
FIG. 14 is a cross sectional view of the bone saw bit of FIG. 13 taken along section line 1A-1A.
Figure 15:
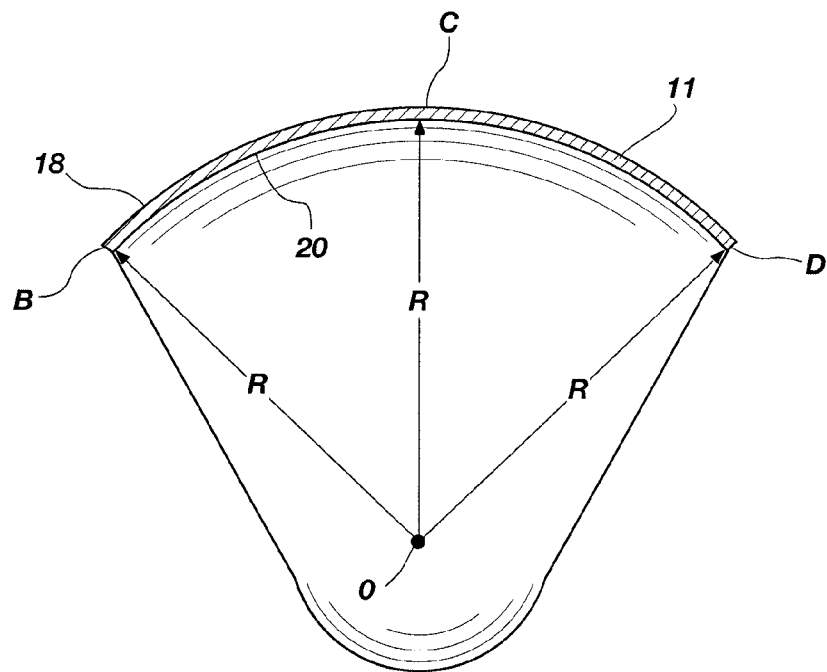
FIG. 15 is a front view of the bone saw bit of FIG. 13.
Figure 16:
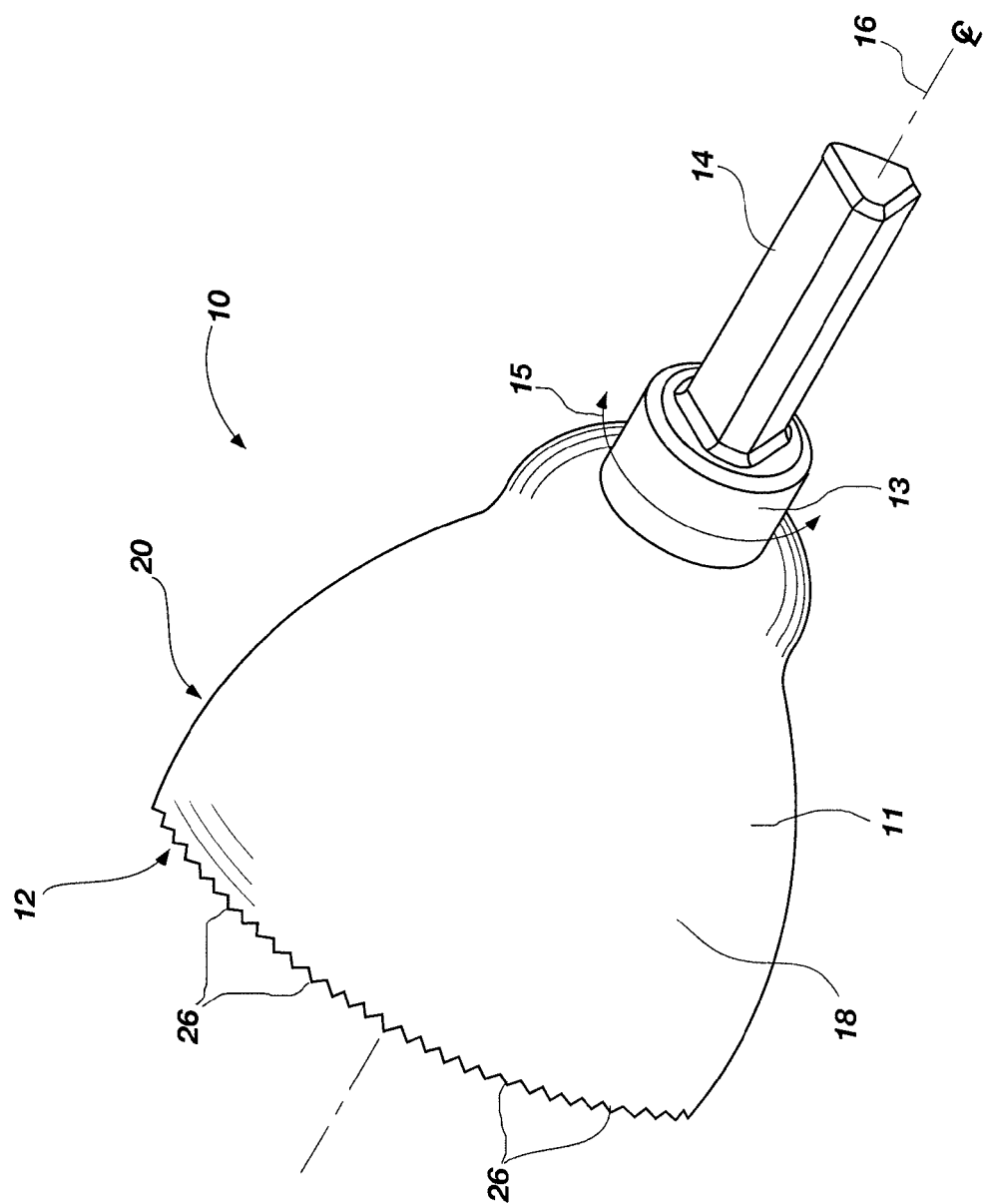
FIG. 16 is another perspective view of the bone saw bit shown in FIG. 13.
Figure 17:
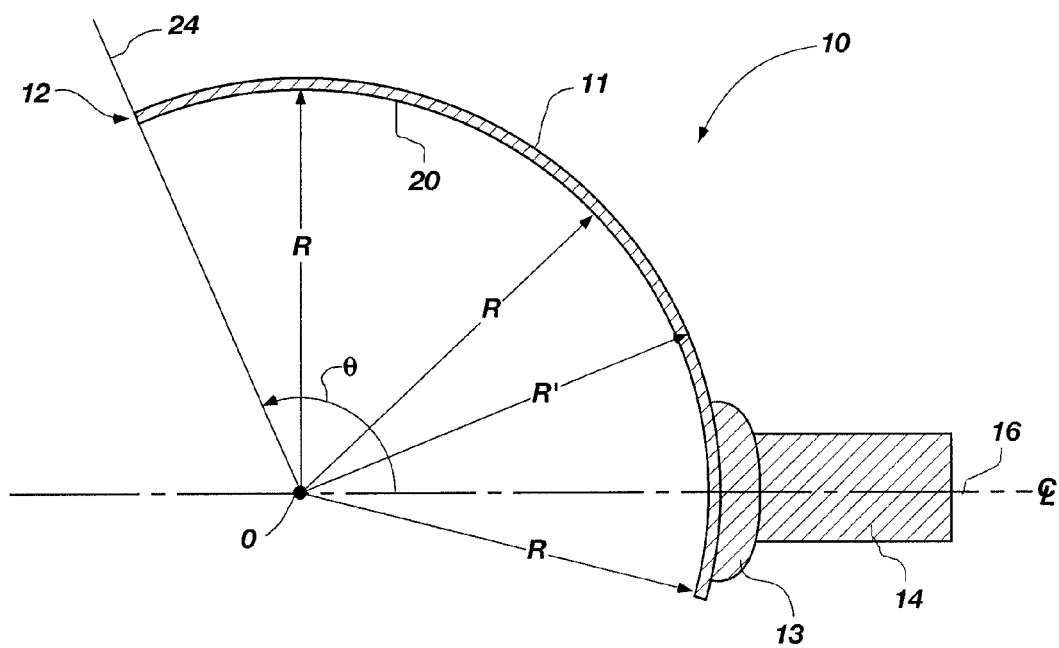
FIG. 17 is a side cross sectional view of a bone saw bit in accordance with the invention.

FIG. 13 is a perspective view of a device, or bone saw bit 10, which may be utilized as an osteotomy device in accordance with the pre-surgical planning method of the instant invention. FIGS. 14 and 15 are further views of the bone saw bit 10. Reference may also be made to FIG. 16 which shows another perspective view of the bone saw bit 10.

The bone saw bit 10 includes a part spherical body 11 and a cutting end 12, which together form key features of the invention. The part spherical body 11 is made of a suitably rigid material such as surgical steel, and may include other materials suitable for the surgical severance of bone, particularly in aseptic environments.

The bone saw bit 10 provides for the efficient surgical sectioning of bone and includes the part spherical body 11 having a shank 14 extending therefrom along an axis 16. The shank 14 allows the bone saw bit 10 to be attached to a chuck e.g., a three-pronged chuck (not shown) of an oscillating saw (not shown). The oscillating saw rotationally drives the bone saw bit 10, as indicated by the double-ended arrow 15 shown in FIG. 16, to efficiently penetrate a desired member, such as bone, in order to obtain an efficient, optimal or "true" dome on both pieces of the severed member. The dome on one severed member will result in a convex dome, while the dome on the other severed member will result in a concave dome.

The shank 14 may have any attachment connection, such as a threaded stem or a quick release, for example without limitation. The attachment connection will allow the bone saw bit 10 to be attached to any device, such as a power tool or hand operated tool for improved cutting control or usability. Also, while the shank 14 is shown as being integral with the part spherical body 11, the shank 14 may also be a separate member that is coupled to the part spherical body 11. Further, the shank 14 may include a hub 13 (see FIG. 14) as shown.

The part spherical body 11 also includes an outer surface 18, an inner surface 20. The cutting end 12 extends between the outer surface 18 and the inner surface 20. The axis 16 may extend axially inline with the shank 14 and passes from the outer surface 18 through the inner surface 20 of the part spherical body 11. The axis 16 includes an epicenter or origin as indicated by indicia O as labeled. The inner surface 20 is substantially characterized by having a constant radius R extending from the epicenter O. Advantageously, the constant radius R allows the bone saw bit 10 to efficiently and smoothly transition over, and rotate about, the member it is cutting. Further, efficient usage of the bone saw bit 10 is provided for because the outer surface 18 may also be substantially characterized by a constant radius R' over the substantial portion thereof, which also advantageously reduces heat generation on the bone caused by friction while helping to prevent necrosis of the bone. Another advantage of the substantially constant radius R of the inner surface 20 and the radius R' of the outer surface 18 is that the bone saw bit 10 is less likely to impinge upon either piece of a bone during cutting thereby avoiding the ill healing effects caused by necrosis.

With reference also to FIG. 15 and continued reference to FIG. 13, the cutting end 12 of the part spherical body 11 extends as an arc BCD that lies substantially within a plane 24 intersecting the epicenter O. The arc BCD has a radius that is substantially equal to the radius "R" of part spherical body 11 allowing a uniform and non-complex cut to be made by the bone saw blade 10. The radius R and radius R' allow the part spherical body 11 to substantially follow precisely within the path made by the cutting end 12 through the bone substantially without impingement thereupon. The dimensional difference between radius R and the radius R' is the thickness of the bone saw blade 11. While the radius of the arc BCD and the radius "R" are substantially equal, it is recognized that they may vary to a slight degree.

Optionally, the cutting end 12 may extend as an arc BCD between the outer surface 18 and the inner surface 20 of the part spherical body 11.

Returning to the bone saw bit 10 of FIG. 13, the bone saw bit 10 has a part spherical body 11. The part spherical body 11 is shaped efficiently to allow the cutting end 12 to engage and cut through a bone at sufficiently steep angle without the bone engaging a substantial portion of the part spherical body 11 or the shank 14 as severance of the bone is completed. In other embodiments, the part spherical body 11 may be contained in less than one hemisphere; in this regard it is a partial or semispherical body. Moreover, the part spherical body 11 may have a shape substantially formed as a spherical triangle, wherein the cutting end 12 is one of the three arcs forming the spherical triangle.

Turning again to FIG. 13, the cutting end 12 comprises a plurality of cutting teeth 26. Each cutting tooth 26 includes oppositely opposed cutting surfaces 27, 28 arranged within a single row. It is to be recognized that other cutting teeth are contemplated within the scope of this invention for example, and without limitation, jagged serration, hyper- or hypo-extending surface edges and multiple rows of cutting teeth. The opposed cutting surfaces 27, 28 of the plurality of cutting teeth are each symmetrically spaced and aligned.

Optionally, the plurality of cutting teeth 26 may also comprise a plurality of inner cutting teeth and a plurality of outer cutting teeth, where the inner cutting teeth each have an inner tooth surface, the inner tooth surface having the radius R of the inner surface 20 of the part spherical body 11, and the outer cutting teeth each having an outer tooth surface, the outer tooth surface congruent with the outer surface 18 of the part spherical body 10.

FIG. 15 shows a schematic representation, circumscribed about a sphere, illustrating a bone saw bit 10 in accordance with another embodiment of the invention. Reference may also be made to FIG. 16. The part spherical body 11 includes an outer surface 18, an inner surface 20, a cutting end 12 extending between the outer surface 18 and the inner surface 20, an axis 16 extending from the outer surface 18 through the inner surface 20, and an epicenter O located on the axis 16. The cutting end 12 extends as an arc lying substantially within a plane, intersecting the epicenter O. An integral shank 14 extends outwardly from the outer surface 18 of the part spherical body 10 and is substantially aligned with and extends parallel to the axis 16.

The part spherical body 11 has a shape substantially formed as a spherical triangle wherein the cutting end 12 is one of the three arcs forming the spherical triangle and the other two arcs are represented by 20.

Figure 18:
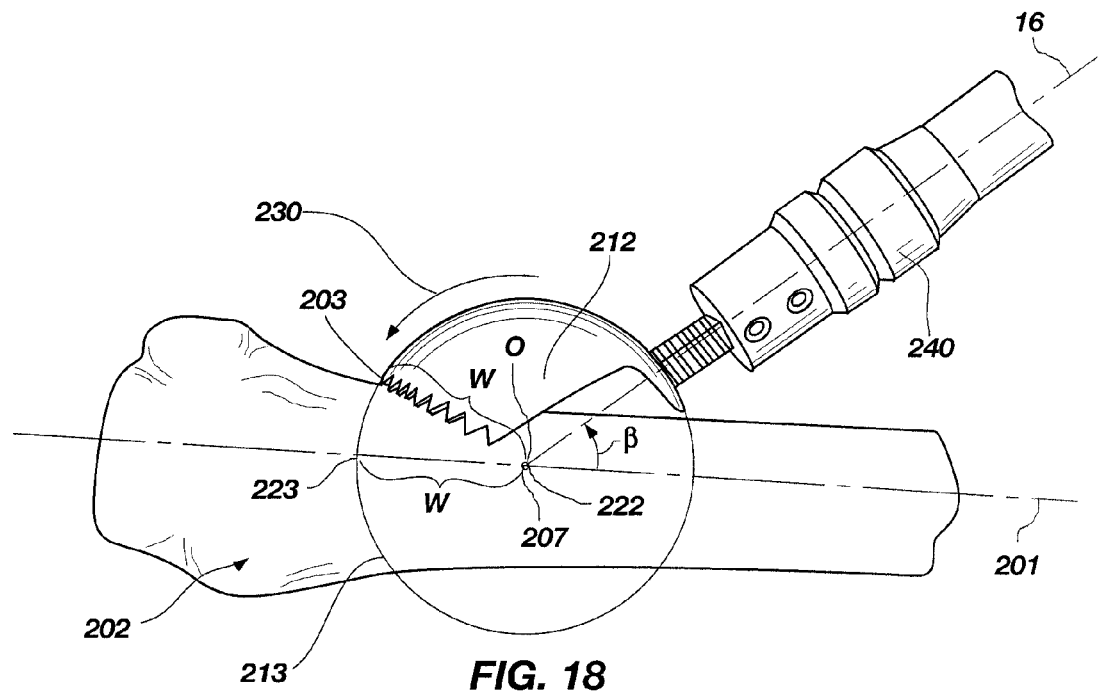
FIG. 18 is a sectional side view of a bone undergoing an osteotomy procedure illustrating an initial stage of the procedure.
Figure 19:
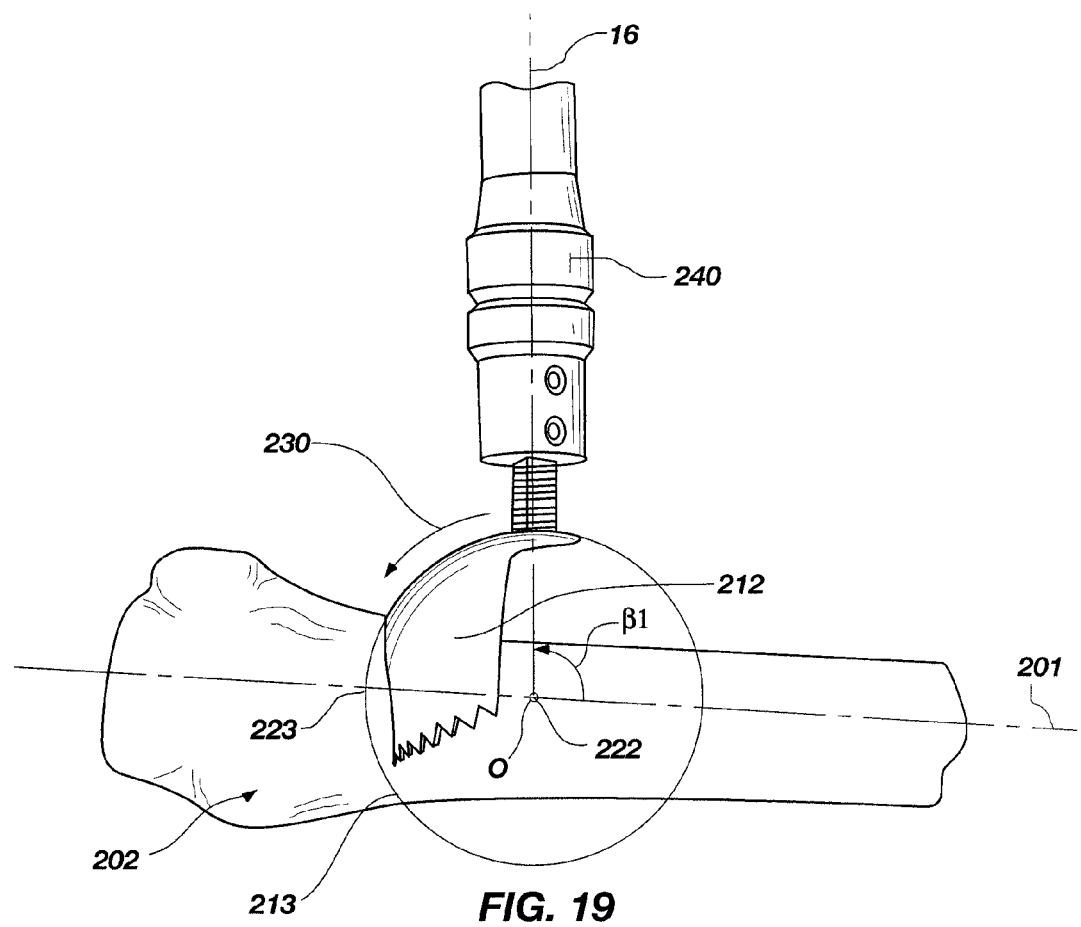
FIG. 19 is a sectional side view of a bone undergoing an osteotomy procedure illustrating an intermediate stage of that procedure.

FIGS. 18-21 illustrate the instant method of performing a sectioning of a bone 202. A bone saw bit 212, as described above with respect to FIG. 13-17, is provided. As previously described the user positions the bone saw bit such that its epicenter O is positioned at the same location as the center of bone correction or 3D CORA. The bone saw bit 212 is positioned on the bone 202 in an orientation and angle 3 predetermined by the surgeon such that the bone saw bit 212 may be rotated as shown by arrow 230 to produce dome height 213. In one embodiment of the invention as illustrated in FIG. 18, the epicenter O of the bone saw bit is positioned at the point 207.

The driver 240, an oscillating or reciprocating saw of a type conventionally associated with surgical saws, is then energized to actuate, i.e., oscillate the cutting end of the bone saw bit 212. The bone saw bit 212 is positioned at the initial angle β determined by the surgeon relative to the center of rotation 222, i.e., the 3D CORA, such that the epicenter O of the bit is positioned on or substantially on the center of rotation 222. Thereafter, the blade is rotated about the center of rotation 222 to cut a path (represented by the dome height 213) by pitching or rotating the driver forward and downward.

In the embodiment of the instant method illustrated in FIGS. 18-21, the center of rotation 222 remains spatially fixed throughout the procedure.

Advantageously, the surgeon will control the orientation of the saw, while the bone saw bit 212 will guide or self-guide and self center itself while making the dome shaped cut between opposing portions 203, 204 of the bone. The procedure is completed when the bone saw bit 212 cuts through the bone 202. In this osteotomy example, bone saw bit 212 is properly sized allowing the positional angle β1 at the beginning of the cut to be approximately 35 to 45 degrees with respect to the longitudinal axis 201 of the bone 202, which allows the bone saw bit 212 to be rotated through about 135 to 145 degrees in order to finish cutting the bone 202.

Figure 20:
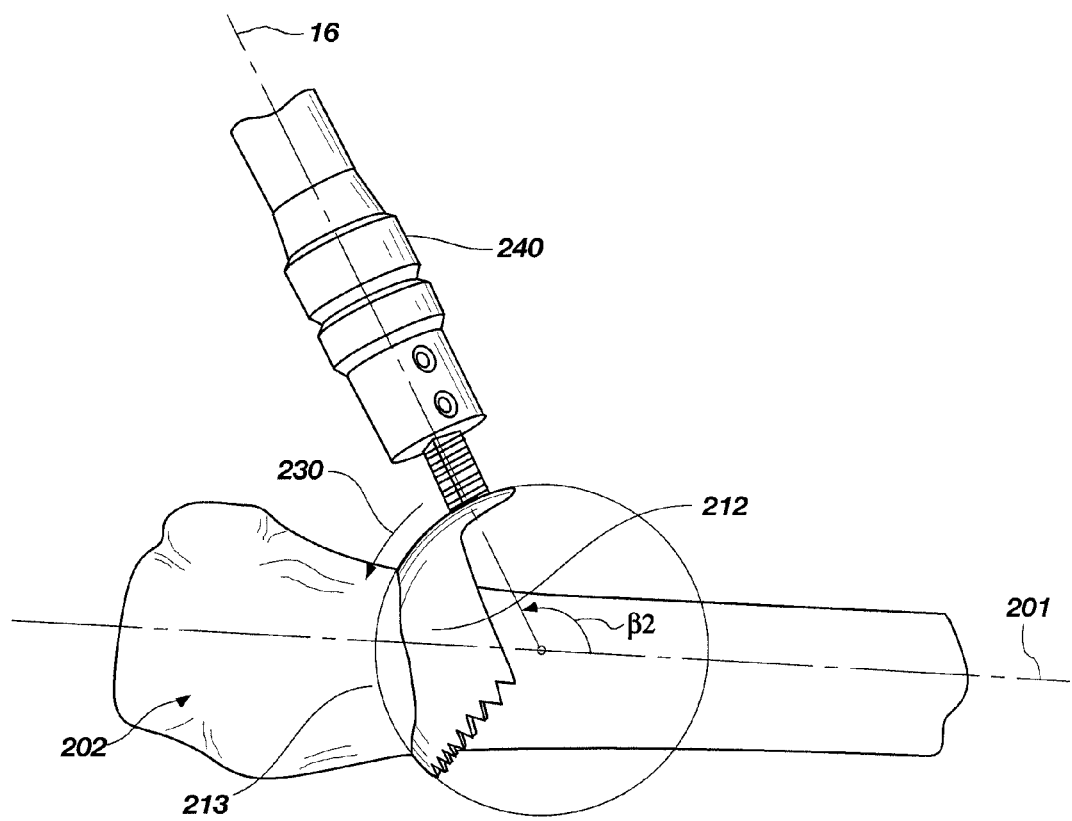
FIG. 20 is a sectional side view of a bone undergoing an osteotomy procedure illustrating a final stage of that procedure.

In order to balance the need for efficient cutting, the need to sever the bone in a single pass and the need to provide three-dimensional adjustment of the bone pieces, the angle of the blade at the conclusion of the cut β2 may be smaller or greater than the 120 degrees illustrated in FIG. 20.

Figure 22:
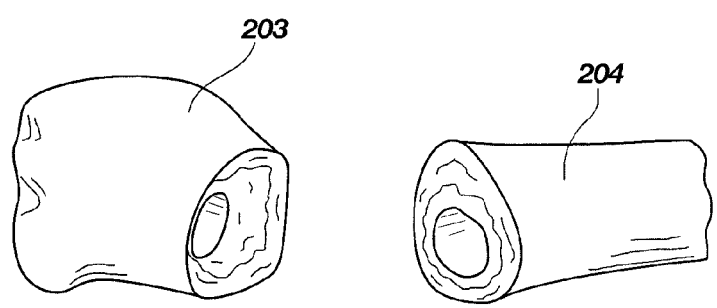
FIG. 22 is a perspective view of a sectioned bone produced under an osteotomy procedure of the instant invention.

FIG. 22 illustrates a bone which has been sectioned into two bone segments utilizing the method of the instant invention.

Figure 23:
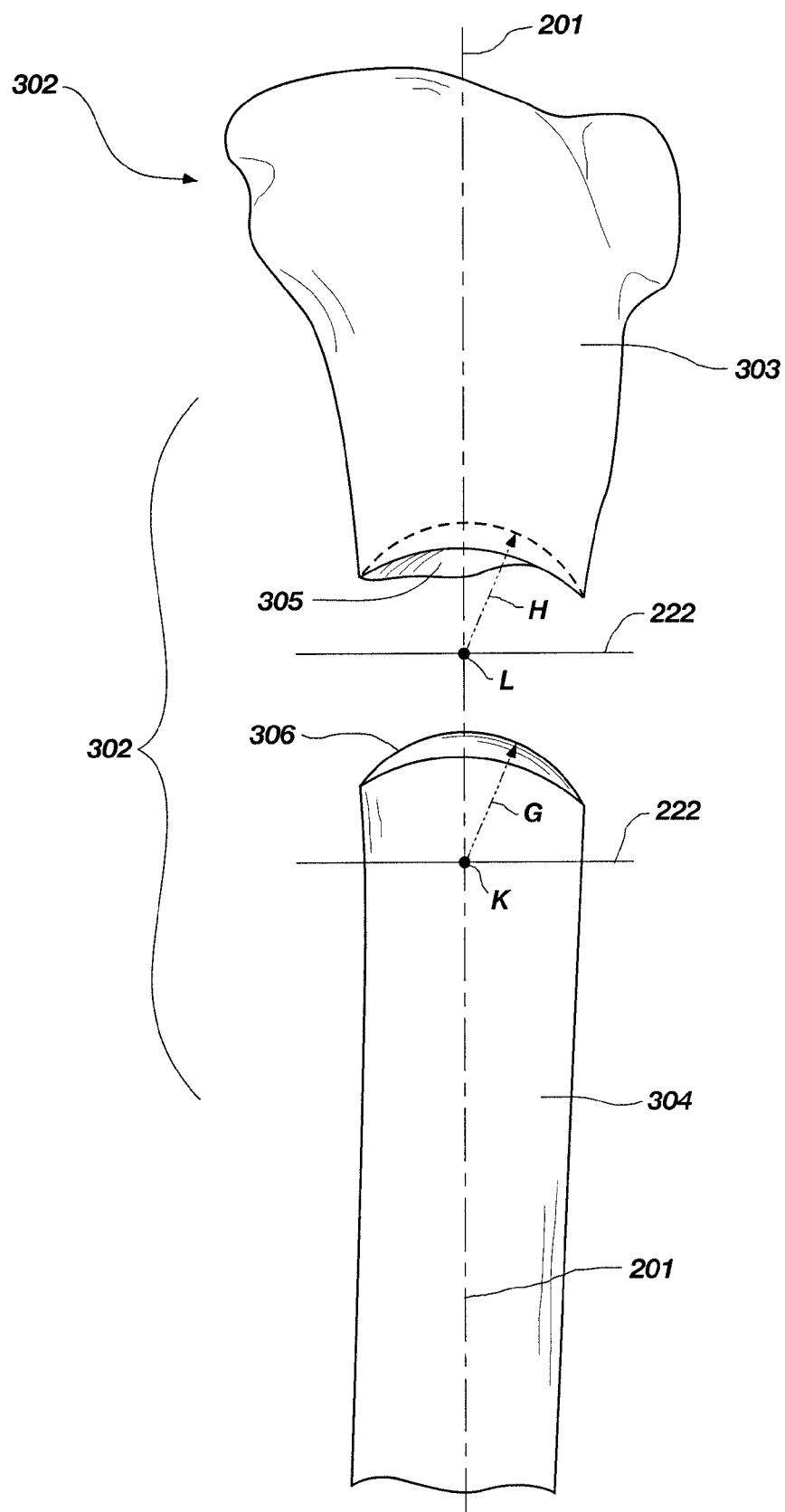
FIG. 23 is an elevational front view of a bone which has undergone an osteotomy procedure of the invention.

FIG. 23 shows two bone portions 303, 304 of a bone 302 having "true dome" or spherical osteotomy surface having been surgically severed with a saw blade bit. Bone portion 303 includes a concave surface 305 defined by the radius J extending from an epicenter L that corresponds to center of rotation 222 and the axis 201 of the bone 303. Bone portion 304 includes a convex surface 306 defined by the radius G extending from an epicenter K that corresponds to central point 222 and the longitudinal axis 201 of the bone 304. It is to be recognized that the epicenters L and K may extend from a location other than the longitudinal axis 201 of the bone or the center of rotation 222 depending upon how the surgeon makes the cut through the bone with a bone saw bit. The bone 302 was severed into bone portions 303, 304 with a bone saw bit in accordance with embodiments of the invention as the surgeon transitioned the bone saw bit about point 222 as described above.

Advantageously, the concave surface 305 substantially mates with the convex surface 306 allowing the bone portions 303, 304 to be repositioned together about any of three degrees of freedom, because the concave surface 305 and the convex surface 306 are both "true dome" or spherical osteotomies that substantially mate. Furthermore, the surgeon may perform the osteotomy by positioning the central point 222, or allowing it to transition, where it is convenient to sever the bone 302, because the "true dome" or spherical osteotomy result is obtained anywhere about the bone, particularly their central axis, when the novel bone saw bit is used.

Besides its use as a guide for providing a surgeon with information to assist in the actual positioning and cutting path for the osteotomy device, the computer simulation can also be used to dimension the size of the blade of the osteotomy device which should be optimally used to perform the osteotomy. The shape and dimensional characteristics of the osteotomy blade, specifically its radius, can be extracted from the computer simulation by reference to the sizing of the respective surface element 390 relative to the respective size of the bone, i.e., its radius, at the location which is to be sectioned. In practice it has been ascertained that the blade of the osteotomy device generally should have a radius which is approximately twice the radius of the bone at the region in which the bone is to be sectioned.

The computerized simulation of the ostoetomy can also be utilized to design and dimension custom orthopedic fixation devices which could be employed, subsequent to the actual sectioning of the bone, to secure the sectioned bone elements one to another. The computer simulation can be used to provide the structural shape and dimensions for such fixation devices and may furthermore be utilized to indicate suggested placement positions for such fixation devices. After obtaining such information regarding the structural characteristics for the fixation devices, the invention also contemplates the use of computer aided manufacturing (CAM) applications to design fixation devices which are uniquely suited for the particular bone being treated.

From the foregoing it can be understood that the invention provides a novel pre-surgical planning method to perform "true dome" or spherical osteotomies. The invention attains several advantages, some of which are summarized as follows:

(1) A method is provided for making a dome shaped cut through a solid substance resulting in two substantially congruent mating surfaces;

(2) A method to perform true dome osteotomies, as opposed to conventional barrel-vault osteotomies, for the purpose of correcting malalignment and malorientation of bones in humans and animals is also provided;

(3) A method to perform improved corrective osteotomies that produce two bone sections with congruent dome shaped mating surfaces that may be realigned and fixed in place;

(4) The method provides for optimal dome height, increased stability of the rejoined bone sections, minimized bone loss, decreased chance of damage to bone tissue and the surrounding soft tissue, a rapid and structurally effective mending or knitting of the bone, faster and more reliable healing, as well as the orthopedic surgeon's ability to make intraoperative adjustments to attain the desired correction, including correcting for large rotational deformities;

(5) The pre-surgical planning method provides, through the use of a computer simulation, the ability to accurately define a three-dimensional sectioning surface which can be translated to the actual bone to be treated for purposes of assisting the surgeon to accurately section the bone at the correct location;

(6) The pre-surgical planning method also permits the surgeon to optimize the subsequent realignment of the sectioned bone segments through the results obtained by pre-surgical computerized simulations; and (7) The use of cardan-type joints, or similar universal joints, located at the centers of bone correction, i.e., 3D CORAs, in these computer simulations, permits the clinician to optimize the angular correction of the bone to be treated, thereby facilitating an optimal realignment configuration for the subject bone.

Changes may be made to the embodiments described in this disclosure without departing from the broad inventive concepts they illustrate. Accordingly, this invention is not limited to the particular embodiments disclosed, but is intended to cover all modifications that are within the scope of the invention as defined by the appended claims.

What is claimed is:

1. A pre-surgical planning method for performing a spherical osteotomy on a bone, the method comprising:
    obtaining a computerized tomography (CT) image of said bone;
    converting said image to a three-dimensional (3D) computerized format;
    utilizing said converted image and a computer to locate a plurality of axes within said image of said bone, each said axis being associated with a respective substantially linear region of said bone;
    identifying at least one center of correction within said bone, each said center of correction being located at an intersection of at least two of said axes;
    locating at least one element, having a surface configured as a portion of a sphere, on said converted image of said bone, an epicenter of said surface of said at least one element being located at a respective said center of correction;
    locating at least one sectioning region on said computerized image of said bone; said sectioning region being defined as an intersection of said surface of said at least one element and said computerized image of said bone;
    locating at least one bone sectioning region on said bone corresponding to said at least one sectioning region on said computerized image of said bone; and
    using an osteotomy device to section said bone along said at least one bone sectioning region.

2. The method of claim 1, wherein said bone sectioning region is configured as a portion of a sphere.

3. The method of claim 1, wherein said osteotomy device includes a cutting element having a shape which defines a portion of a sphere.

4. The method of claim 1, wherein said osteotomy device has a cutting edge which is arcuate in configuration.

5. The method of claim 1, wherein said osteotomy device defines an axis of rotation and wherein said bone is cut by the action of a cutting portion of said osteotomy device oscillating about said axis of rotation.

6. The method of claim 5, wherein said method further includes:
    positioning said cutting portion of said osteotomy device in an initial position with respect to said bone;
    oscillating the cutting portion of said osteotomy device about said axis of rotation; and thereafter, rotating the cutting portion of the osteotomy device from the initial position to a final position, about said center of correction.

7. The method of claim 1, wherein said three-dimensional computerized format is a three-dimensional computer assisted design (CAD) format.

8. The method of claim 1, further comprising utilizing said computer to section said computerized image of said bone into individual segments.

9. The method of claim 8, further comprising utilizing said computer to join said individual segments together.

10. The method of claim 9, wherein said computer is programmed to position cardan type joints at the respective centers of correction.

11. The method of claim 10, further comprising displacing said individual segments, relative to one another, and utilizing said cardan joints to align said individual segments relative to one another.

12. The method of claim 11, wherein at least one of said cardan joints is constructed to permit a user to independently angulate a first said individual segment about a respective said cardan joint in a frontal plane and a sagital plane and rotate said first individual segment about a respective said axis thereof.

13. The method of claim 12, wherein said at least one cardan joint is constructed to permit a first angular adjustment of said first individual segment in one projection and thereafter facilitate a second angular adjustment of a second individual segment in a second projection without said second angular adjustment effecting said first angular adjustment.

14. The method of claim 13, further comprising further adjusting angles of at least one said cardan joint to obtain a medically acceptable overall configuration of said bone.

15. The method of claim 1, further comprising isolating images of said bone to be treated.

16. The method of claim 1, further comprising utilizing a plurality of views of said three-dimensional CAD format to locate said axes.

17. The method of claim 1, further comprising identifying at least one point of intersection of at least two of said axes and denominating said at least one intersection as a center of bone correction or 3D CORA.

18. The method of claim 17, further comprising utilizing the computer to locate at least one feature at said at least one point of intersection.

19. The method of claim 18, further comprising utilizing the computer to define an intersection of said surface and the 3D representation of the bone thereby defining a three-dimensional sectioning surface.

20. The method of claim 19, further comprising simulating a sectioning of the bone along one or more of the intersections of the of the spherical surfaces and the bone thereby producing a computer representation of a plurality of segmented bone elements.

21. The method of claim 20, further comprising programming said computer to position cardan type joints at said points of intersection and utilizing said cardan type joints to displace said sectioned bone elements relative to one another in order to spatially orient the bone elements with respect to one another to obtain an acceptable overall simulated alignment of said bone elements.

22. The method of claim 21, further comprising providing an actual solid model of the bone to be treated.

23. The method of claim 22, further comprising replicating said computer simulated sectioning of the bone.

24. The method of claim 21, further comprising identifying and locating the center of bone correction in the actual bone to be treated.

25. The method of claim 24, further comprising utilizing the computer simulated sectioning of the bone to position a cutting edge of an osteotomy device in such a way that an epicenter of a blade element of the osteotomy device is at or substantially at the same location as the center of bone correction or 3D CORA.

26. The method of claim 24, further comprising utilizing the computer simulated sectioning of the bone to position a cutting edge of an osteotomy device in such a way that an epicenter of a blade element of the osteotomy device is at offset from the center of bone correction or 3D CORA.

27. The method of claim 25, further comprising realigning the bone element produced by said sectioning of said bone to be treated, utilizing the computer simulation as a guide to produce a realigned bone having the configuration suggested by the computer simulation.

28. The method of claim 1, further comprising utilizing said computer to identify structural characteristics of an osteotomy device for use in performing said sectioning procedure.

29. The method of claim 1, further comprising utilizing said computer to identify structural characteristics of fixation devices for use in securing bone elements, produced by said sectioning procedure, to one another.

30. The method of claim 29, wherein said computer, in association with a computer aided manufacturing application (CAM) is utilized to design and manufacture orthopedic fixation devices for use in securing said bone elements to one another after a sectioning of said bone.

31. The method of claim 3, wherein said osteotomy device includes a cutting element and an axis, said cutting element being configured for oscillation about said axis.

32. The method of claim 1, wherein each axis radiating from a said center of correction is disposed in a single common plane, each center of correction having a centerline of rotation, oriented orthogonal to said single common plane, associated therewith;
wherein a cutting element of said osteotomy device is rotated about a said centerline of rotation as said osteotomy device cuts said bone along said bone sectioning region.

33. The method of claim 3, further comprises:
positioning said cutting element of said osteotomy device in an initial position with respect to said bone, wherein a center point of said portion of a sphere of said cutting element is disposed on a said center of correction.

34. The method of claim 1, further comprises:
oscillating a cutting portion of said osteotomy device about an axis of rotation of said osteotomy device; and thereafter,
rotating the cutting element of the osteotomy device from an initial position to a final position, about said center of correction.

35. The method of claim 34, wherein a centerline of rotation passes through the center of correction associated with a single common plane.

36. The method of claim 1, wherein the osteotomy device comprises a blade element which defines a portion of a spherical body, said portion of a spherical body comprising an outer surface;

an inner surface; and a cutting end, extending between the outer surface and the inner surface, said cutting end defining an arc;

said arc being disposed at a common radial distance over a length thereof from an epicenter of said portion of a spherical body.

* * * * *